(12) United States Patent
Dhinsa et al.

(10) Patent No.: US 12,390,305 B2
(45) Date of Patent: Aug. 19, 2025

(54) ORTHODONTIC TREATMENT TRACKING METHODS AND SYSTEMS

(71) Applicant: Tooth Fairy Healthcare Ltd, London (GB)

(72) Inventors: Kian Dhinsa, Walsall (GB); Aulak Deepak, Wolverhampton (GB)

(73) Assignee: Tooth Fairy Healthcare Ltd, London (GB)

( * ) Notice: Subject to any disclaimer, the term of this patent is extended or adjusted under 35 U.S.C. 154(b) by 584 days.

(21) Appl. No.: 17/626,717

(22) PCT Filed: Jul. 13, 2020

(86) PCT No.: PCT/SG2020/050400
§ 371 (c)(1),
(2) Date: Jan. 12, 2022

(87) PCT Pub. No.: WO2021/010895
PCT Pub. Date: Jan. 21, 2021

(65) Prior Publication Data
US 2022/0257340 A1    Aug. 18, 2022

(30) Foreign Application Priority Data
Jul. 12, 2019   (GB) ...................................... 1910027

(51) Int. Cl.
*A61C 7/00*    (2006.01)
*A61C 9/00*    (2006.01)
(Continued)

(52) U.S. Cl.
CPC ............ *A61C 7/002* (2013.01); *A61C 9/0053* (2013.01); *A61C 13/34* (2013.01); *G06T 7/0016* (2013.01);
(Continued)

(58) Field of Classification Search
CPC ....... A61C 7/002; A61C 9/0053; A61C 13/34; G06T 7/74; G06T 7/75; G06T 7/0016; G16H 30/40
See application file for complete search history.

(56) References Cited

U.S. PATENT DOCUMENTS 5,605,459 A * 2/1997 Kuroda .................. A61C 7/002
                                                                433/68
10,478,269 B2 * 11/2019 Jin ......................... A61C 7/002
(Continued)

FOREIGN PATENT DOCUMENTS

CN      106504321 A      3/2017
EP      3409183 A1       12/2018
(Continued)

OTHER PUBLICATIONS

International Search Report and Written Opinion of the International Searching Authority issued in PCT/SG2020/050400, mailed Nov. 19, 2020; ISA/EP.
(Continued)

*Primary Examiner* — David Bilodeau
(74) *Attorney, Agent, or Firm* — Harness, Dickey & Pierce, P.L.C.

(57) ABSTRACT

Methods and systems for tracking orthodontic treatment are disclosed. In an embodiment, an orthodontic treatment tracking method for tracking progress of a tooth alignment treatment comprises: receiving a patients mouth image; comparing the patients mouth image with a tooth alignment treatment checkpoint image to determine if the tooth alignment treatment has reached a treatment checkpoint; and generating an alignment treatment progress indication indicating whether the tooth alignment treatment has reached the treatment checkpoint.

17 Claims, 5 Drawing Sheets

(51) Int. Cl.
  *A61C 13/34* (2006.01)
  *G06T 7/00* (2017.01)
  *G06T 7/73* (2017.01)
  *G16H 30/40* (2018.01)

(52) U.S. Cl.
  CPC .................. *G06T 7/74* (2017.01); *G06T 7/75* (2017.01); *G16H 30/40* (2018.01); *G06T 2207/30036* (2013.01)

(56) References Cited

U.S. PATENT DOCUMENTS

| | | |
|---|---|---|
| 2007/0134613 A1 | 6/2007 | Kuo et al. |
| 2008/0305454 A1 | 12/2008 | Kitching et al. |
| 2013/0231899 A1* | 9/2013 | Khardekar .............. G06F 30/00 703/1 |
| 2013/0308843 A1* | 11/2013 | Tank .......... G06T 7/12 382/128 |
| 2015/0348320 A1* | 12/2015 | Pesach .................. A61C 9/006 382/128 |
| 2017/0103569 A1 | 4/2017 | Wu et al. |
| 2017/0105814 A1* | 4/2017 | Lim ...................... A61C 7/148 |
| 2018/0078128 A1 | 3/2018 | Adamson et al. |
| 2018/0168781 A1 | 6/2018 | Kopelman et al. |
| 2018/0235437 A1* | 8/2018 | Ozerov ................ A61B 5/4552 |
| 2019/0026893 A1 | 1/2019 | Salah et al. |
| 2020/0066391 A1* | 2/2020 | Sachdeva ............... G16H 20/40 |
| 2021/0113089 A1 | 4/2021 | Kopelman et al. |
| 2023/0210453 A1* | 7/2023 | Brawn .................... A61C 7/00 433/6 |

FOREIGN PATENT DOCUMENTS

| | | |
|---|---|---|
| KR | 20160149301 A | 12/2016 |
| WO | WO-2009006273 A1 | 1/2009 |

OTHER PUBLICATIONS

International Preliminary Report on Patentability (Chapter II of the Patent Cooperation Treaty), mailed Sep. 20, 2021; IPEA EP.

Examination Report for corresponding United Kingdom Application No. GB1910027.0 issued Dec. 5, 2022; 4 pages.

* cited by examiner

ORTHODONTIC TREATMENT TRACKING METHODS AND SYSTEMS

CROSS REFERENCE TO RELATED APPLICATIONS

This application is a U.S. National Phase Application under 35 U.S.C. 371 of International Application No. PCT/SG2020/050400 filed on Jul. 13, 2020, which claims the benefit of priority from Great Britain Patent Application No. 1910027.0 filed on Jul. 12, 2019. The entire disclosures of all of the above applications are incorporated herein by reference.

TECHNICAL FIELD

The present disclosure relates to methods and systems for tracking orthodontic treatment and in particular to the tracking of tooth alignment treatment.

BACKGROUND

Tooth alignment treatment typically involves a patient wearing an aligner device which applies a pressure to specific teeth and this pressure causes a gradual movement of those teeth. A treatment program typically involves the patient using a set of aligner devices in sequence. The current norm is to change aligners every two weeks, however the rate of movement can vary between patients. Currently patients have to visit or consult with a dentist or orthodontist to determine whether they are using the correct aligner in the sequence or if they should move on to the next aligner. Often the dentist will determine the positions of the patient's teeth by eye in order to judge whether the patient should move on to the next aligner in the sequence.

This can lead to inaccurate timing to the patient moving through the sequence of aligners and there is also a requirement for the patient to make many visits to the dentist or orthodontist to monitor the orthodontic treatment.

SUMMARY

According to a first aspect of the present disclosure, an orthodontic treatment tracking method for tracking progress of a tooth alignment treatment is provided. The method comprises: receiving a patient's mouth image; comparing the patient's mouth image with a tooth alignment treatment checkpoint image to determine if the tooth alignment treatment has reached a treatment checkpoint; and generating an alignment treatment progress indication indicating whether the tooth alignment treatment has reached the treatment checkpoint.

Embodiments of the present invention allow the progress of alignment treatment to be scientifically tracked, rather than relying on arbitrary time lengths or assessment by eye. By tracking the progress of the orthodontic treatment, the treatment can potentially be made quicker as the patient is able to switch to the next aligner in the sequence without having to wait until their next visit to the dentist or the arbitrary two week time period has elapsed. Tracking can also avoid changing the aligner at the wrong time, if the positions of the teeth in the patient's mouth are not ready for the next aligner, this can cause excessive force on teeth which may cause pain. Further, the method allows remote tracking, less visits to the dentist may be required. Further, patients tracking the treatment may result in better compliance with the treatment, the patients may be more likely to engage and therefore achieve the completed treatment. By accurately tracking movement during treatment and identifying the best time to change aligner device, we will be able to decrease the duration each aligner device is worn for, significantly decreasing treatment times.

In an embodiment, the treatment checkpoint is a patient tooth position corresponding to a progression between tooth alignment devices and the alignment progress indication comprises an indication to change tooth alignment devices if the alignment treatment has reached the treatment checkpoint.

Comparing the patient's mouth image with a tooth alignment treatment checkpoint image may comprise determining a current tooth position indicative shape from the patient's mouth image, determining a treatment checkpoint tooth position indicative shape from the treatment checkpoint image and comparing the current tooth position indicative shape with the treatment checkpoint tooth position indicative shape.

The patient's mouth image is a two-dimensional image and may be captured with a portable electronic device.

In an embodiment, the method further comprises generating the tooth alignment treatment checkpoint image from a three-dimensional model tooth model.

In an embodiment, the method further comprises performing an image transformation on the patient's mouth image and/or the tooth alignment treatment checkpoint image. The image transformation may be a rescaling and/or a rotation.

The alignment treatment progress indication may indicate a percentage of progress to the treatment checkpoint. The alignment treatment progress indication may further comprise an indication of a time period until the treatment checkpoint is reached.

According to a second aspect of the present disclosure a method of capturing a patient's mouth image on a user device is provided. The method comprises: displaying an indicative shape overlaid on a camera view; capturing a patient's mouth image; and sending the patient's mouth image to an orthodontic treatment tracking system.

The indicative shape may indicate the arches of the jaws of the patient.

In an embodiment, the method further comprises determining that the patient's mouth image was captured within a correct range of orientation angles.

According to a third aspect of the present disclosure, a computer readable medium storing computer executable instructions which when executed on a processor cause the processor to carry out a method as described above is provided.

According to a fourth aspect of the present disclosure an orthodontic treatment tracking system for tracking progress of a tooth alignment treatment is provided. The system comprises a processor and a data storage device. The data storage device stores computer program instructions operable to cause the processor to: receive a patient's mouth image; compare the patient's mouth image with a tooth alignment treatment checkpoint image to determine if the tooth alignment treatment has reached a treatment checkpoint; and generate an alignment treatment progress indication indicating whether the tooth alignment treatment has reached the treatment checkpoint.

In an embodiment, the treatment checkpoint is a patient tooth position corresponding to a progression between tooth alignment devices and the alignment progress indication comprises an indication to change tooth alignment devices if the alignment treatment has reached the treatment checkpoint.

In an embodiment, the data storage device further stores computer instructions operable to cause the processor to compare the patient's mouth image with a tooth alignment treatment checkpoint image by determining a current tooth position indicative shape from the patient's mouth image, determining a treatment checkpoint tooth position indicative shape from the treatment checkpoint image and comparing the current tooth position indicative shape with the treatment checkpoint tooth position indicative shape.

The patient's mouth image may be a two-dimensional image. The patient's mouth image may be captured by a portable electronic device.

In an embodiment, the data storage device further stores computer instructions operable to cause the processor to generate the tooth alignment treatment checkpoint image from a three-dimensional model tooth model.

In an embodiment, the data storage device further stores computer instructions operable to cause the processor to perform an image transformation on the patient's mouth image and/or the tooth alignment treatment checkpoint image. The image transformation may comprise a resealing and/or a rotation.

The alignment treatment progress indication may indicate a percentage of progress to the treatment checkpoint. The alignment treatment progress indication may further comprise an indication of a time period until the treatment checkpoint is reached.

According to a fifth aspect of the present disclosure a user device is provided. The user device is configured to: display an indicative shape of a mouth overlaid on a camera view; capture a patient's mouth image; and send the patient's mouth image to an orthodontic treatment tracking system.

In an embodiment, the user device is further configured to determine that the patient's mouth image was captured within a correct range of orientation angles.

BRIEF DESCRIPTION OF THE DRAWINGS

In the following, embodiments of the present invention will be described as non-limiting examples with reference to the accompanying drawings in which.

DETAILED DESCRIPTION

Figure 1:
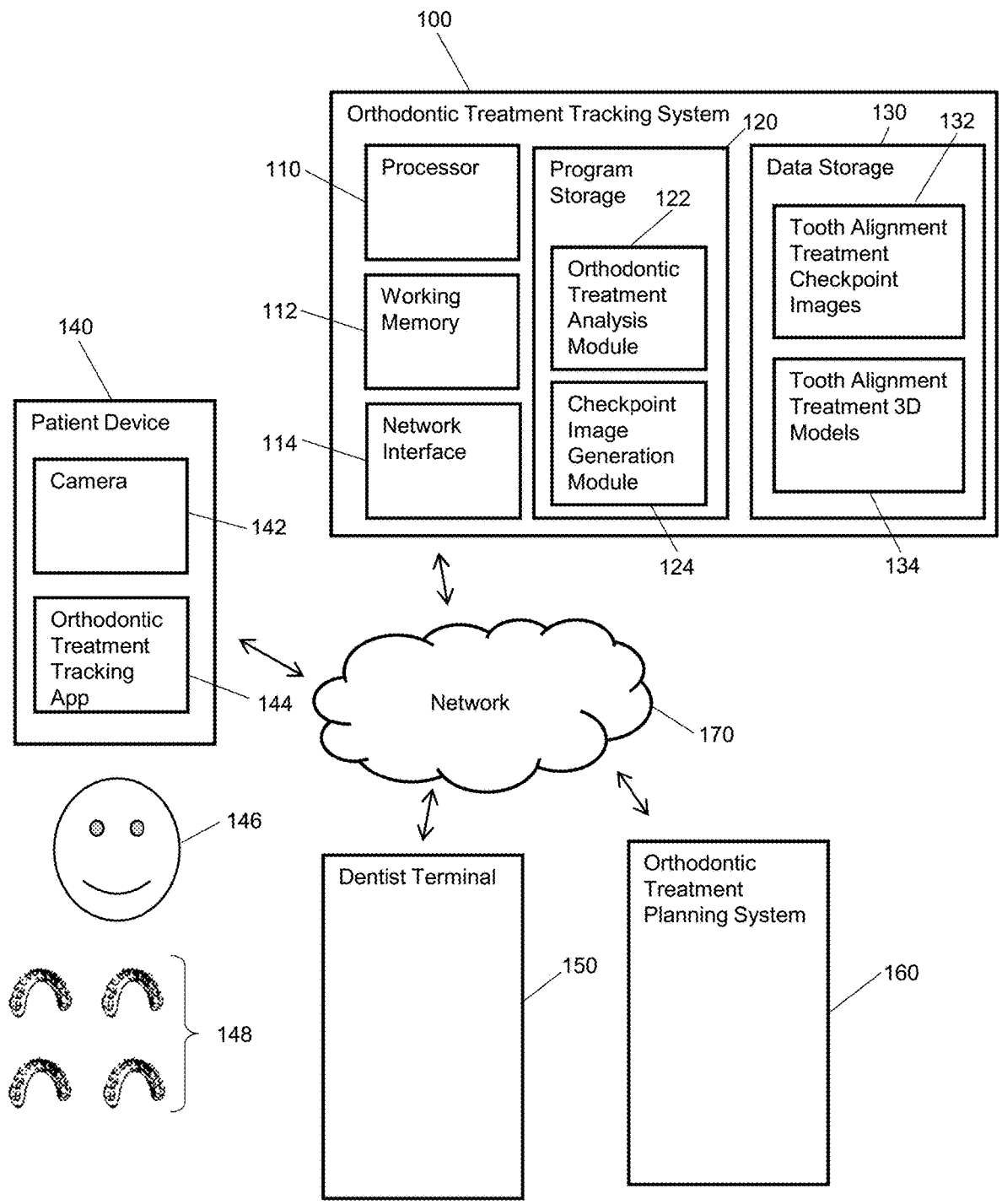
FIG. 1 is a block diagram showing a system for tracking orthodontic treatment according to an embodiment of the present invention.

FIG. 1 is a block diagram showing a system for tracking orthodontic treatment according to an embodiment of the present invention. As shown in FIG. 1, the orthodontic treatment tracking system 100 is coupled to a patient device 140, a dentist terminal 150 and an orthodontic treatment planning system 160 by a network 170.

The orthodontic treatment tracking system 100 tracks the progress of an orthodontic treatment which is carried out on a patient 146. The orthodontic treatment involves the patient 146 wearing aligners 148 in sequence to reposition one or more of the patient's teeth. The orthodontic treatment is planned by the orthodontic treatment planning system 160. The planning of the orthodontic treatment may be automated or alternatively, the planning may be carried out by a professional such as a dentist, orthodontist, therapist, treatment planner or technician. The process involves capturing a three-dimensional model of the initial positions of the teeth of the patient 146. The three-dimensional model may be captured by an intraoral scanner or may be generated from a dental impression of the patient's teeth or may be generated from images captured of the patient's teeth or from bite registration paste. A final three-dimensional model of the teeth of the patient 146 is then generated by the orthodontic treatment system 160. This final 3d model shows the target teeth in their final positions after the orthodontic treatment has been completed. The orthodontic treatment planning system 160 generates a set of tooth alignment treatment 3d models. These 3d models form a sequence of positions of the teeth between the initial positions of the teeth of the patient and the final positions in the final three-dimensional model. The set of aligners 148 are generated from the tooth alignment treatment 3d models. The orthodontic treatment involves the patient 146 wearing the aligners 148 in sequence to cause the teeth of the patient 146 to move from the initial positions to the final positions.

A typical orthodontic treatment involves the patient wearing a sequence of aligners with each aligner being worn for 2 weeks. Each aligner of the sequence is intended to move the tooth or teeth being treated to a target position. The timing of the patient switching from one aligner to the next should occur once a tooth or teeth under treatment have reached the target position for the aligner. Embodiments of the present invention allow tracking of the movement of the patient's teeth during orthodontic treatment and thus the accurate timing of the switching of aligners can be matched to the unique movement of the individual patient's teeth. This therefore can potentially speed up treatment times.

The patient 146 captures an image of their teeth using the camera 142 of the patient device 140 under the control of an orthodontic treatment tracking app 144 running on the patient device 140. The patient device 140 may be a mobile telephone device. The patient's mouth image captured by the camera 142 of the patient device 140 is sent by the orthodontic treatment tracking app 144 running on the patient device 140 to the orthodontic treatment tracking system 100. The orthodontic treatment tracking system 100 compares a patient's mouth image with a treatment tracking image and determines whether the tooth or teeth of the patient have reached a checkpoint position. If the tooth or teeth have reached the checkpoint position, then an alignment treatment progress indication indicating that the patient should move on to the next aligner in the sequence is generated. If the tooth or teeth have not yet reached the checkpoint position, then an alignment treatment progress indication indicating that that patient should continue to wear the current aligner is generated.

The orthodontic treatment tracking system 100 is a computer system with a memory that stores computer program modules which implement orthodontic treatment tracking methods according to embodiments of the present invention.

The orthodontic treatment tracking system 100 comprises a processor 110, a working memory 112, a network interface 114, program storage 120 and data storage 130. The processor 110 may be implemented as one or more central processing unit (CPU) chips. The program storage 120 is a non-volatile storage device such as a hard disk drive which stores computer program modules. The computer program modules are loaded into the working memory 112 for execution by the processor 110. The network interface is an interface which allows data, for received signal strength indicator data sets to be received by the machine learning localization system 100. The network interface 114 may be a wireless network interface such as a Wi-Fi or Bluetooth interface, alternatively it may be a wired interface.

The program storage 120 stores an orthodontic treatment analysis module 122 and a checkpoint image generation module 124. The computer program modules cause the processor 110 to execute various orthodontic treatment tracking processing which is described in more detail below. The program storage 120 may be referred to in some contexts as computer readable storage media and/or non-transitory computer readable media. As depicted in FIG. 1, the computer program modules are distinct modules which perform respective functions implemented by the orthodontic treatment tracking system 100. It will be appreciated that the boundaries between these modules are exemplary only, and that alternative embodiments may merge modules or impose an alternative decomposition of functionality of modules. For example, the modules discussed herein may be decomposed into sub-modules to be executed as multiple computer processes, and, optionally, on multiple computers. Moreover, alternative embodiments may combine multiple instances of a particular module or sub-module. It will also be appreciated that, while a software implementation of the computer program modules is described herein, these may alternatively be implemented as one or more hardware modules (such as field-programmable gate array(s) or application-specific integrated circuit(s)) comprising circuitry which implements equivalent functionality to that implemented in software.

The data storage 130 stores tooth alignment treatment checkpoint images 132 and tooth alignment treatment 3d models 134. The tooth alignment treatment checkpoint images 132 are images of the projected locations of the patient's teeth when the alignment treatment reaches a checkpoint at which the patient should change from one aligner to the next aligner in the sequence. The tooth alignment treatment 3d models 134 are three-dimensional models of the patient's teeth at each stage of the tooth alignment treatment.

The tooth alignment treatment 3d models 134 are generated by the orthodontic treatment planning system 160 as part of the process of planning the patient's treatment and producing the set of aligners 148 for the patient 146. The tooth alignment treatment checkpoint images 132 may be generated from the tooth alignment treatment 3d models 134 by the checkpoint image generation module 124. This process may take place during an initialization phase, for example when the tooth alignment treatment 3d models 134 are received by the orthodontic treatment tracking system 100 from the orthodontic treatment planning system 160. Alternatively, the generation of the tooth alignment treatment checkpoint images 132 may take place as part of an orthodontic treatment tracking method. In some embodiments the checkpoint images may be created without the need to create 3d models.

The dentist terminal 150 is connected to the orthodontic treatment tracking system 100 by the network 170 and allows a dentist or orthodontist to manage the orthodontic treatment tracking carried out by the orthodontic treatment tracking system 100. In some embodiments, the dentist may be able to interact with the patient 146 though the orthodontic treatment tracking system 100. In some embodiments, the output of the orthodontic treatment tracking method carried out by the orthodontic treatment tracking system 100 may be provided to the dentist for review before being provided to the patient 146, or the output may be provided to the dentist and then the dentist may communicate the output to the patient 146. In some embodiments, the dentist may be able to control or supervise the capture of the patient's mouth image by the camera 142 of the patient device 140. This allows the dentist to ensure that the captured image includes the required view of the patient's teeth.

Figure 2:
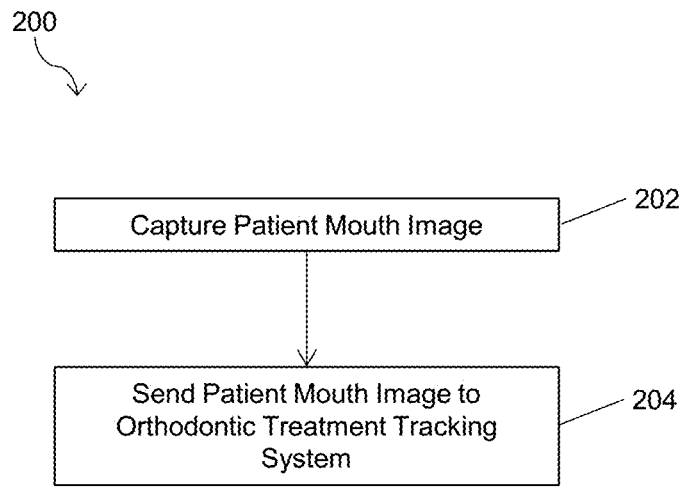
FIG. 2 is a flowchart showing a method of capturing a patient's mouth image for use in an orthodontic treatment tracking method according to an embodiment of the present invention.

FIG. 2 is a flowchart showing a method of capturing a patient's mouth image for use in an orthodontic treatment tracking method according to an embodiment of the present invention. The method 200 shown in FIG. 2 is carried out by the patient device 140 shown in FIG. 1.

The patient may initially input an indication of the aligner that they are currently using at the beginning of the process. This is used by the orthodontic treatment tracking system to identify the most relevant checkpoint model to compare against.

In step 202, the camera 142 of the patient device 140 captures a mouth image of the patient 146. Step 202 may comprise a display of the patient device 140 displaying a template or outline of teeth overlaid over the view of the camera 142 to guide the patient 146 in capturing the patient's mouth image at a correct angle. The patient's mouth image may be a 'bird's eye' view of the lower jaw teeth of the patient. Alternatively, the patient's mouth image may be a different view; an example of a patient's mouth images from a different view is shown in FIGS. 6A-D below. In some embodiments, the orthodontic treatment tracking app 144 running on the patient device 140 may analyze the captured image to determine whether the mouth image was captured at a correct angle and the view of the teeth is unobstructed by objects such as the patient's tongue. In some embodiments, a dentist operating the dentist terminal 150 may be allowed to control the camera 142 of the patient device 140 by the orthodontic treatment tracking app 144 and thus the dentist may control the capture of the image when the correct view of the patient's mouth is in front of the camera 142.

In step 204, the orthodontic treatment tracking app 144 sends the captured patient's mouth image to the orthodontic treatment tracking system 100 over the network 170.

Figure 3:
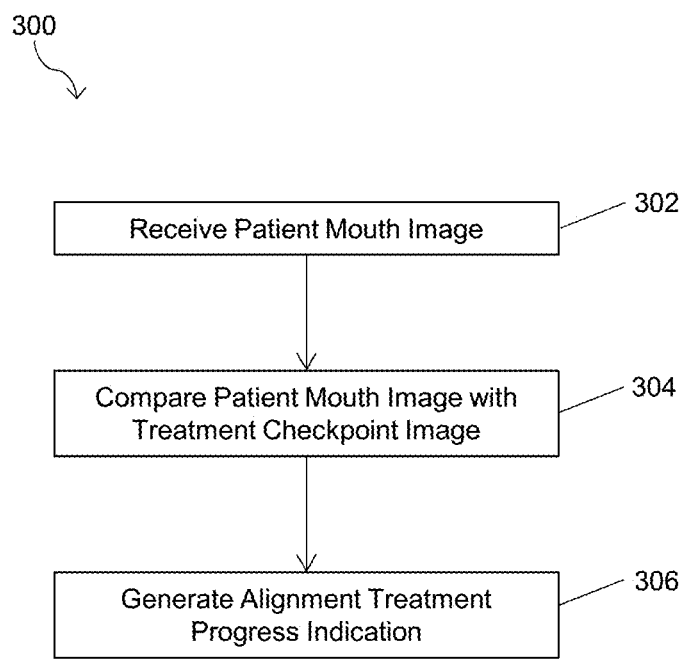
FIG. 3 is a flowchart showing an orthodontic treatment tracking method according to an embodiment of the present invention.

FIG. 3 is a flowchart showing an orthodontic treatment tracking method according to an embodiment of the present invention. The method 300 shown in FIG. 3 is carried out by the orthodontic treatment tracking system 100 shown in FIG. 1.

In step 302, the network interface 114 of the orthodontic treatment tracking system 100 receives the patient's mouth image from the patient device 140. As described above, the patient's mouth image is an image showing the patient's teeth which are undergoing an orthodontic treatment. In some embodiments, an indication of the current aligner being used by the patient may also be received with the patient's mouth image.

In step 304, the orthodontic treatment analysis module 122 is executed by the processor 110 of the orthodontic treatment tracking system 100 to compare the patient's mouth image with one of the tooth alignment treatment checkpoint image 132 stored in the data storage 130 of the orthodontic treatment tracking system 100. The tooth alignment treatment checkpoint images 132 each correspond to the tooth position in which the patient 146 should move to a subsequent aligner of the aligners 148. Thus, the comparison of the patient's mouth image with the tooth alignment treatment checkpoint image corresponding to the aligner which the patient is currently using determines whether the teeth of the patient have moved to the position of that aligner, in which case, the patient 146 should switch to the next aligner in the sequence or whether the teeth of the patient 146 have not yet reached that position in which case the patient should continue to use the current aligner. In some embodiments, an indication of the aligner that the patient is currently using may be received with the patient's mouth image and the relevant tooth alignment treatment checkpoint image 132 is selected according to the indication of the aligner which the patient is currently using. Alternatively, the tooth alignment treatment checkpoint image 132 may be automatically selected by the orthodontic treatment tracking system 100 by analyzing the patient's mouth image. For example, the patient's mouth image may be used to search through a plurality of checkpoint images and the closest checkpoint image may be selected for the comparison.

In step 306, the orthodontic treatment analysis module 122 is executed by the processor 110 to generate an alignment treatment progress indication. The alignment treatment progress indication indicates whether the patient should continue to use the current aligner or switch to using the next aligner. In some embodiments, the alignment treatment progress indication may indicate the amount of progress to the next aligner, this may be as a percentage—for example it may indicate that the patient's teeth have moved 50% of the distance to the next checkpoint. The alignment treatment progress indication may be generated as a message which is sent to the patient device 140 for display to the patient. Alternatively, or additionally, the alignment treatment progress indication may be sent to the dentist terminal 150, to inform the dentist of the result of the orthodontic treatment tracking.

FIG. 4A to FIG. 4H show an example of the comparison of a patient's mouth image with a treatment checkpoint image according to an embodiment of the present invention. The example comparison shown in FIG. 4A to FIG. 4H corresponds to an example implementation of step 304 of the method 300 shown in FIG. 3.

Figure 4A:
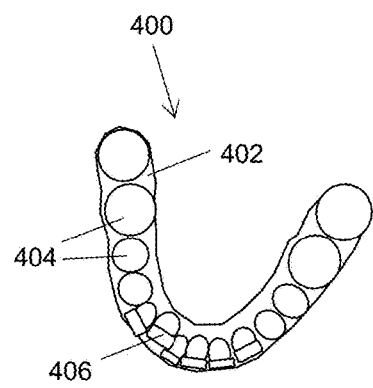
FIG. 4A to FIG. 4H show an example of the comparison of a patient's mouth image with a treatment checkpoint image according to an embodiment of the present invention.

FIG. 4A shows an example of a patient's mouth image. As shown in FIG. 4A, the example patient's mouth image 400 shows the gums 402 and teeth 404 of the patient. As shown in FIG. 4A the patient has a crooked tooth 406 which is out of alignment with the other teeth. During an alignment treatment, the patient wears a series of alignment devices which apply pressure to this tooth to move it into alignment with the other teeth. The patient's mouth image 400 is a two-dimensional image of the patient's mouth which was captured using the patient device 140 shown in FIG. 1.

Figure 4B:
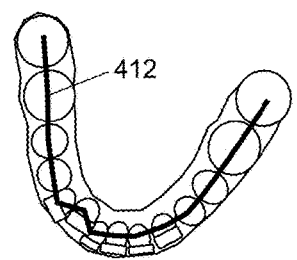

FIG. 4B shows the generation of a current tooth position indicative shape from the patient's mouth image shown in FIG. 4A. As shown in FIG. 4B, the current tooth position inductive shape 412 indicates the relative positions of the teeth of the patient. The current tooth position indicative shape may be determined from the patient's mouth image 400 by identifying the outlines of the teeth of the patient and then determining the center of each tooth and then determining the current tooth position indicative shape by joining the center positions of each tooth. The outlines of the teeth may be identified by applying an image recognition algorithm which identifies the patient's teeth from the color relative to the color of the soft tissues of the patient. Here the soft tissues include the lips, tongue cheeks, gums and hard palate of the patient. Pixel color recognition between white for the teeth and red or pink for the soft tissues may be used to distinguish the teeth. Alternatively, an edge detection algorithm may be applied and the teeth identified by recognizing the shape of the patients gums and teeth from edges in the patient's mouth image.

Figure 4C:
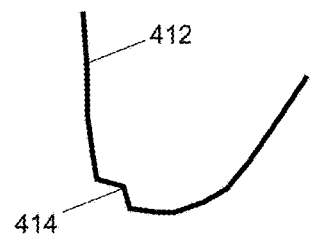

FIG. 4C shows the current tooth position indicative shape. As shown in FIG. 4C, the current tooth position indicative shape 412 indicates the relative position of the patient's teeth. The current tooth position indicative shape 412 includes a deviation 414 from a smooth curve which corresponds to the position of the crooked tooth 406 shown in FIG. 4A.

Figure 4D:
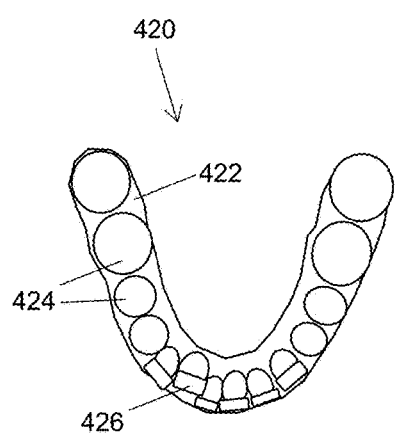

FIG. 4D shows a tooth alignment treatment checkpoint image. The tooth alignment treatment checkpoint image 420 shown in FIG. 4D corresponds to a treatment checkpoint. The tooth alignment checkpoint image 420 may be generated from one of the tooth alignment treatment 3d models 134 shown in FIG. 1. The tooth alignment checkpoint image 422 shows the positions of the patient's teeth 424 and the patient's gums 422. The tooth alignment checkpoint image 420 shows the position of the crooked tooth 426 at the treatment checkpoint.

Figure 4E:
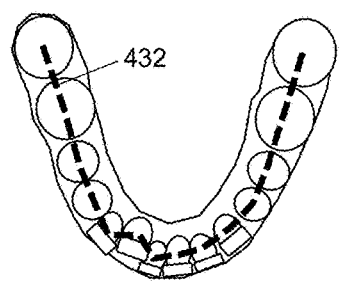

FIG. 4E shows the generation of a treatment checkpoint tooth position indicative shape from the tooth alignment treatment checkpoint image shown in FIG. 4D. As shown in FIG. 4E, the treatment checkpoint tooth position indicative shape 432 indicates the relative positions of the teeth at the specific treatment checkpoint. As with the current tooth position indicative shape, the treatment checkpoint tooth position indicative shape 432 may be determined from the tooth alignment treatment checkpoint image 420 by identifying the outlines of the teeth, then determining the center of each tooth and then determining the treatment checkpoint tooth position indicative shape by joining the center positions of each tooth. The outlines of the teeth may be identified by applying an image recognition algorithm which identifies the patient's teeth from the color relative to the color of the gums of the patient. Alternatively, an edge detection algorithm may be applied, and the teeth identified by recognizing the shape of the patients gums and teeth from edges in the patient's mouth image.

Figure 4F:
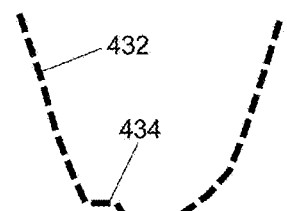

FIG. 4F shows the treatment checkpoint tooth position indicative shape. As shown in FIG. 4F, the treatment checkpoint tooth position indicative shape 432 indicates the relative position of the teeth at the treatment checkpoint. The treatment checkpoint tooth position indicative shape 432 includes a deviation 434 from a smooth curve which corresponds to the position of the crooked tooth 416 shown in FIG. 4D. To perform the comparison, the whole curve or part of the curve may be used.

Figure 4G:
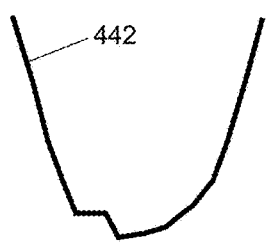

FIG. 4G shows the current tooth position indicative shape following a transformation. It is noted that the orientation and scale of the current tooth position indicative shape 412 shown in FIG. 4C may be different from the orientation and scale of the treatment checkpoint tooth position indicative shape 432 shown in FIG. 4F. Thus, a transform including a rotation and a scaling may be applied to either the current tooth position indicative shape 412 or the treatment checkpoint tooth position indicative shape 432 to allow a comparison. The transform may be determined by comparing the overall shape of the current tooth position indicative shape 412 and the treatment checkpoint tooth position indicative shape 432. It is noted that there is no change to the teeth at the rear of the patient's mouth during this example orthodontic alignment treatment, thus overall shapes of the current tooth position indicative shape 412 and the treatment checkpoint tooth position indicative shape 432 can be compared to determine the transform.

In the example shown in FIG. 4G, a transformed current tooth position indicative shape 442 is generated.

Figure 4H:
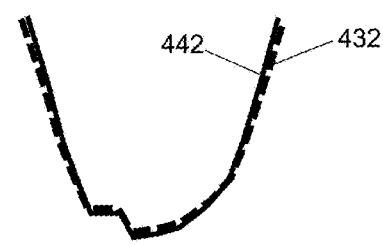

FIG. 4H shows a comparison of the transformed current tooth position indicative shape 442 and the treatment checkpoint tooth position indicative shape 432. In order to determine whether the crooked tooth 406 has reached the treatment checkpoint, a similarity measure between the transformed current tooth position indicative shape 442 and the treatment checkpoint tooth position indicative shape 432 may be calculated and compared with a threshold. If the similarity measure exceeds the threshold, then the orthodontic treatment is determined to have reached the checkpoint and an alignment treatment progress indication indicating that the orthodontic treatment has reached the checkpoint is generated and the patient upon receiving this begins to use the next tooth alignment device in the sequence.

FIG. 5A to FIG. 5H show an example of the comparison of a patient's mouth image with a treatment checkpoint image according to an embodiment of the present invention.

Figure 5A:
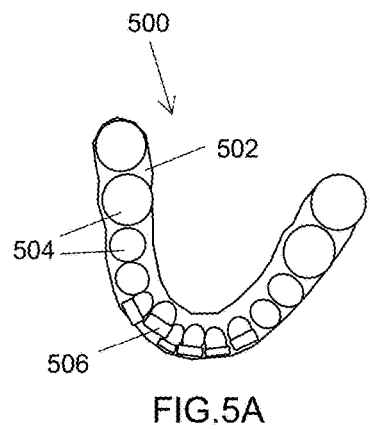
FIG. 5A to FIG. 5H show an example of the comparison of a patient's mouth image with a treatment checkpoint image according to an embodiment of the present invention.

FIG. 5A shows an example of a patient's mouth image. As shown in FIG. 5A, the example patient's mouth image 500 shows the gums 502 and teeth 504 of the patient. As in the example described above with reference to FIG. 4A, the patient has a crooked tooth 506 which is out of alignment with the other teeth.

Figure 5B:
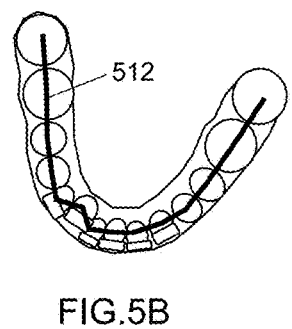

FIG. 5B shows the generation of a current tooth position indicative shape from the patient's mouth image shown in FIG. 5A. As shown in FIG. 5B, the current tooth position indicative shape 512 indicates the relative positions of the teeth of the patient. The current tooth position indicative shape may be determined as described above with reference to FIG. 4B.

Figure 5C:
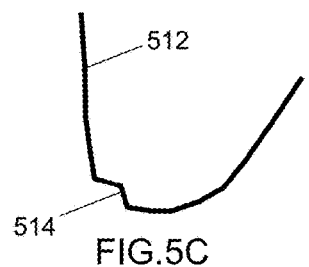

FIG. 5C shows the current tooth position indicative shape. As shown in FIG. 5C, the current tooth position indicative shape 512 indicates the relative position of the patient's teeth. The current tooth position indicative shape 512 includes a deviation 514 from a smooth curve which corresponds to the position of the crooked tooth 506 shown in FIG. 5A.

Figure 5D:
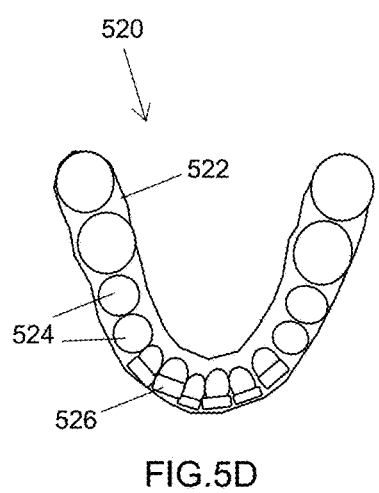

FIG. 5D shows a tooth alignment treatment checkpoint image. The tooth alignment treatment checkpoint image 520 shown in FIG. 5D corresponds to a treatment checkpoint later in the tooth alignment treatment than the treatment checkpoint image 420 shown in FIG. 4D. The tooth alignment checkpoint image 520 is generated from a subsequent one of the tooth alignment treatment 3d models 134 shown in FIG. 1. The tooth alignment checkpoint image 522 shows the positions of the patient's teeth 524 and the patient's gums 522. The tooth alignment checkpoint image 520 shows the position of the crooked tooth 526 at the treatment checkpoint. As can be seen from FIG. 5D, the position of the crooked tooth 526 is in closer alignment with the other teeth than the position of the crooked tooth 426 shown in FIG. 4D.

Figure 5E:
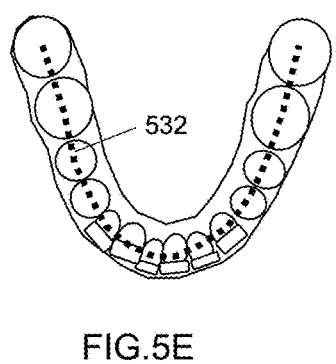

FIG. 5E shows the generation of a treatment checkpoint tooth position indicative shape from the tooth alignment treatment checkpoint image shown in FIG. 5D. As shown in FIG. 5E, the treatment checkpoint tooth position indicative shape 532 indicates the relative positions of the teeth at the specific treatment checkpoint. As described above, the treatment checkpoint tooth position indicative shape 532 may be determined from the tooth alignment treatment checkpoint image 520 by identifying the outlines of the teeth, then determining the center of each tooth and then determining the treatment checkpoint tooth position indicative shape by joining the center positions of each tooth. The outlines of the teeth may be identified by applying an image recognition algorithm which identifies the patient's teeth from the color relative to the color of the gums of the patient. Alternatively, an edge detection algorithm may be applied and the teeth identified by recognizing the shape of the patients gums and teeth from edges in the patient's mouth image.

Figure 5F:
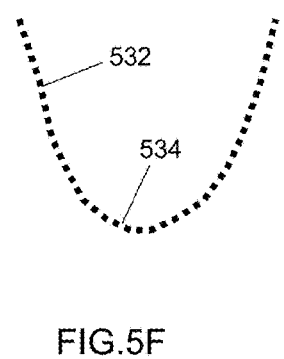

FIG. 5F shows the treatment checkpoint tooth position indicative shape. As shown in FIG. 5F, the treatment checkpoint tooth position indicative shape 532 indicates the relative position of the teeth at the treatment checkpoint. The treatment checkpoint tooth position indicative shape 532 includes a much smaller deviation 534 from a smooth curve which corresponds than the treatment checkpoint tooth position indicative shape 432 shown in FIG. 4F.

Figure 5G:
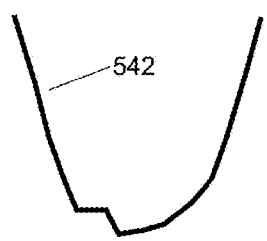

FIG. 5G shows the current tooth position indicative shape following a transformation. As described above, a transformed current tooth position indicative shape 542 is generated by applying a transform which may include a rotation and a scaling to the current tooth position indicative shape 512 shown in FIG. 5C.

Figure 5H:
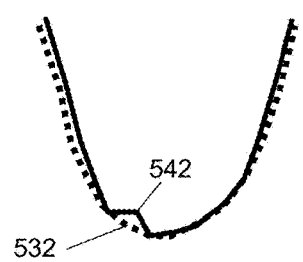

FIG. 5H shows a comparison of the transformed current tooth position indicative shape 542 and the treatment checkpoint tooth position indicative shape 532. In order to determine whether the crooked tooth 506 has reached the treatment checkpoint, a similarity measure between the transformed current tooth position indicative shape 542 and the treatment checkpoint tooth position indicative shape 532 may be calculated and compared with a threshold. In this example, there is a significant difference between the transformed current tooth position indicative shape 542 and the treatment checkpoint tooth position indicative shape 532. Thus, the crooked tooth 506 has not reached the treatment checkpoint. Therefore, an alignment treatment progress indication indicating that the orthodontic treatment has not reached the checkpoint is generated and the patient upon receiving this continues to use the current tooth alignment device.

In the example described above, tooth position indicative shapes are determined from the patient's mouth image and the tooth alignment treatment checkpoint image as the midlines of the teeth in each image. In an alternative embodiment, the outlines of the teeth are compared to determine if the orthodontic treatment has reached the checkpoint. A combination of different techniques may be used in the comparison.

FIG. 6A to FIG. 6D show examples of patient's mouth images and tooth alignment treatment checkpoint images used in embodiments of the present invention.

Figure 6A:
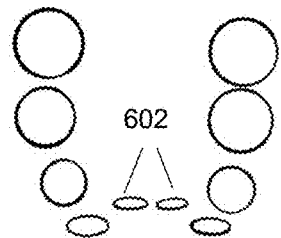
FIG. 6A to FIG. 6D show examples of patient's mouth images and tooth alignment treatment checkpoint images used in embodiments of the present invention.

FIG. 6A shows a patient's mouth image which is a top-down or bird's eye view. As shown in FIG. 6A, the patient's mouth image 600 shows the positions of the patient's teeth, including two teeth 602 undergoing alignment treatment.

Figure 6B:
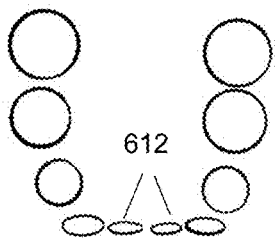

FIG. 6B shows a tooth alignment treatment checkpoint image which is a top-down or bird's eye view. As shown in FIG. 6B, the tooth alignment treatment checkpoint image 610 shows the checkpoint positions of the patient's teeth, including the positions of the two teeth 612 undergoing alignment treatment.

Figure 6C:
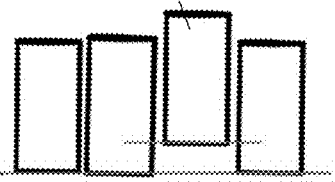

FIG. 6C shows a patient's mouth image which is a frontal view showing movement in a vertical manner. As shown in FIG. 6C, the patient's mouth image 650 shows the vertical positions of the patient's teeth, including a tooth 652 undergoing alignment treatment which is displaced above the line 654 of the other teeth.

Figure 6D:
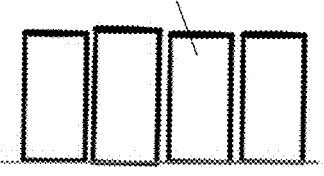

FIG. 6D shows a tooth alignment treatment checkpoint image which is a frontal view. As shown in FIG. 6D, the tooth alignment treatment checkpoint image 660 shows the checkpoint positions of the patient's teeth, including the position of the tooth 662 undergoing alignment treatment.

The comparison process for the patient's mouth image 600 shown in FIG. 6A with the tooth alignment treatment checkpoint image 610 shown in FIG. 6B may take place as described above with reference to FIG. 4A to FIG. 4H and FIG. 5A to FIG. 5H.

Examples of possible comparison processes for the patient's mouth image 650 shown in FIG. 6C with the tooth alignment treatment checkpoint image 6160 shown in FIG. 6D will now be described with reference to FIG. 7A to FIG. 7D.

FIG. 7A to FIG. 7D show examples of the comparison of a patient's mouth image with a tooth alignment treatment checkpoint image according to embodiments of the present invention.

Figure 7A:
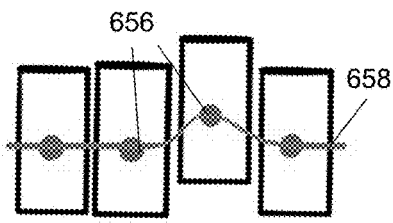
FIG. 7A to FIG. 7D show examples of the comparison of a patient's mouth image with a treatment checkpoint image according to embodiments of the present invention.
Figure 7B:
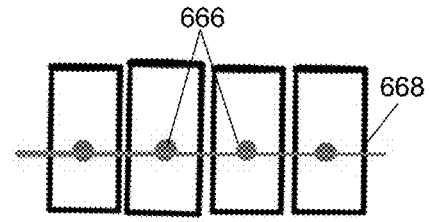

As shown in FIG. 7A and FIG. 7B, the comparison may take place by determining a mid-point 656 of each tooth and then forming a tooth midpoint line 658 for the patient's mouth image. Similarly, a mid-point 666 of each tooth is determined for the tooth alignment treatment checkpoint image, and a checkpoint tooth mid-point line 668 is determined. The tooth mid-point line 658 and the checkpoint tooth mid-point line 668 are compared to determine whether the movement of the tooth under treatment has reached the checkpoint.

Figure 7C:
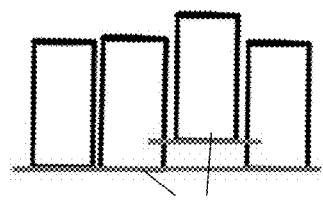
Figure 7D:
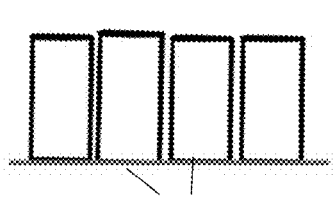

As shown in FIG. 7C and FIG. 7D, the comparison may take place by comparing the position of the tooth under alignment treatment with the position of other teeth. Color and image recognition is used to distinguish between the gum and tooth of the patient and the lower edges 756 (incisal edges) of the patient's teeth is identified in the patient's mouth image. Similarly, color and image recognition is used to identify the lower edges 766 (incisal edges) of the teeth in the tooth alignment treatment checkpoint image. The lower edges 756 of the teeth in the patient's mouth image are compared with the lower edges 766 of the teeth in the tooth alignment treatment checkpoint image to determine whether the movement of the tooth under treatment has reached the checkpoint. Alternatively, the teeth shape formed by the patient's teeth in the patient's mouth image may be compared with the teeth shape formed by the teeth in the tooth alignment treatment checkpoint image In the examples described above, the patient's mouth image is a two-dimensional image of the teeth in the patient's mouth that are undergoing an alignment treatment. Embodiments are envisaged in which a three-dimensional image is captured by the patient device, for example, the patient device may include a depth sensor such as a light detection and ranging (LIDAR) sensor. In some embodiments, the patient device may capture a video sequence including multiple views of the patient's teeth and a representative patient's mouth image may be generated from this video sequence.

In the examples described above, the orthodontic treatment involves a set of aligners and the treatment checkpoints correspond to the patient switching between the aligners. Other possible orthodontic treatments which may be monitored using embodiments of the present invention include tooth realignment with fixed braces. In this case, the method may be used to determine if the fixed braces require wire readjustment to advance the tooth realignment treatment.

In some embodiments, a comparison using one of the methods described above may be performed between the patient's mouth image and two tooth alignment treatment checkpoint images: a checkpoint image corresponding to the start point of alignment treatment using the current alignment device, and a checkpoint image corresponding to the end point of alignment treatment using the current alignment device. For example if the patient is currently using the third aligner in the sequence, the start checkpoint image corresponds to the third aligner and the end checkpoint image corresponds to the fourth aligner in the sequence. In these embodiments, the progress of the alignment treatment may be determined as a percentage or fraction of progress from the results of the comparisons with the two tooth alignment treatment checkpoint images. The alignment treatment progress indication may be generated by comparing the percentage with a threshold. For example, once the tooth movement is determined to be 90% or 9/10 of the movement to the end checkpoint image, the alignment treatment progress indication may indicate that the patient should move to the next alignment device. The alignment treatment progress indication may include an indication of the percentage or fraction of progress to the end checkpoint. For example, the alignment treatment progress indication may indicate that the movement of the patient's teeth under treatment is 60% of the movement to the end checkpoint under the current aligner device. This may be used to estimate the number of days until the need to switch to the next aligner in the sequence.

Whilst the foregoing description has described exemplary embodiments, it will be understood by those skilled in the art that many variations of the embodiments can be made within the scope and spirit of the present invention.

The invention claimed is:

1. An orthodontic treatment tracking method for tracking progress of a tooth alignment treatment, the method comprising:
   receiving a patient's mouth image captured by a mobile communication device;
   comparing the patient's mouth image with a tooth alignment treatment checkpoint image by:
      determining a current tooth position indicative shape from the patient's mouth image, wherein the current tooth position indicative shape comprises a line representing relative positions of neighboring teeth in the patient's mouth image;
      determining a treatment checkpoint tooth position indicative shape from the tooth alignment treatment checkpoint image, wherein the treatment checkpoint tooth position indicative shape comprises a line representing relative positions of neighboring teeth in the tooth alignment treatment checkpoint image; and
      comparing the current tooth position indicative shape with the treatment checkpoint tooth position indicative shape to determine if the tooth alignment treatment has reached a treatment checkpoint; and
   generating an alignment treatment progress indication indicating whether the tooth alignment treatment has reached the treatment checkpoint.

2. A method according to claim 1, wherein the treatment checkpoint is a patient tooth position corresponding to a progression between tooth alignment devices and the alignment progress indication comprises an indication to change tooth alignment devices if the alignment treatment has reached the treatment checkpoint.

3. A method according to claim 1, wherein the patient's mouth image is a two-dimensional image.

4. A method according to claim 1, further comprising generating the tooth alignment treatment checkpoint image from a three-dimensional tooth model.

5. A method according to claim 1, further comprising performing an image transformation on the patient's mouth image and/or the tooth alignment treatment checkpoint image.

6. A method according to claim 5, wherein the image transformation comprises an image rescaling and/or an image rotation.

7. A method according to claim 1, wherein the alignment treatment progress indication indicates a percentage of progress to the treatment checkpoint.

8. A method according to claim 7, wherein the alignment treatment progress indication further comprises an indication of a time period until the treatment checkpoint is reached.

9. A non-transitory computer readable medium storing computer executable instructions which when executed on a processor causes the processor to carry out a method according to claim 1.

10. An orthodontic treatment tracking system for tracking progress of a tooth alignment treatment, the system comprising a processor and a data storage device, the data storage device storing computer program instructions operable to cause the processor to:
receive a patient's mouth image captured by a mobile communication device;
compare the patient's mouth image with a tooth alignment treatment checkpoint image by:
determining a current tooth position indicative shape from the patient's mouth image, wherein the current tooth position indicative shape comprises a line representing relative positions of neighboring teeth in the patient's mouth image;
determining a treatment checkpoint tooth position indicative shape from the treatment checkpoint image, wherein the treatment checkpoint tooth position indicative shape comprises a line representing relative positions of neighboring teeth in the tooth alignment treatment checkpoint image; and
comparing the current tooth position indicative shape with the treatment checkpoint tooth position indicative shape to determine if the tooth alignment treatment has reached a treatment checkpoint; and
generate an alignment treatment progress indication indicating whether the tooth alignment treatment has reached the treatment checkpoint.

11. An orthodontic treatment tracking system according to claim 10, wherein the treatment checkpoint is a patient tooth position corresponding to a progression between tooth alignment devices and the alignment progress indication comprises an indication to change tooth alignment devices if the alignment treatment has reached the treatment checkpoint.

12. An orthodontic treatment tracking system according to claim 10, wherein the patient's mouth image is a two-dimensional image.

13. An orthodontic treatment tracking system according to claim 10, wherein the data storage device further stores computer instructions operable to cause the processor to generate the tooth alignment treatment checkpoint image from a three-dimensional model tooth model.

14. An orthodontic treatment tracking system according to claim 10, wherein the data storage device further stores computer instructions operable to cause the processor to perform an image transformation on the patient's mouth image and/or the tooth alignment treatment checkpoint image.

15. An orthodontic treatment tracking system according claim 14, wherein the image transformation comprises an image rescaling and/or an image rotation.

16. An orthodontic treatment tracking system according to claim 10, wherein the alignment treatment progress indication indicates a percentage of progress to the treatment checkpoint.

17. An orthodontic treatment tracking system according claim 16, wherein the alignment treatment progress indication further comprises an indication of a time period until the treatment checkpoint is reached.

* * * * *